US006629996B2

(12) United States Patent
Baikoff

(10) Patent No.: US 6,629,996 B2
(45) Date of Patent: Oct. 7, 2003

(54) ANTERIOR CHAMBER INTRAOCULAR IMPLANT

(76) Inventor: Georges Baikoff, 317 Corniche Kennedy, 13007 Marseilles (FR)

( * ) Notice: Subject to any disclaimer, the term of this patent is extended or adjusted under 35 U.S.C. 154(b) by 0 days.

(21) Appl. No.: 09/801,219

(22) Filed: Mar. 7, 2001

(65) Prior Publication Data

US 2002/0026241 A1 Feb. 28, 2002

Related U.S. Application Data

(63) Continuation of application No. PCT/FR99/02126, filed on Sep. 7, 1999.

(51) Int. Cl.[7] .................................................. A61F 2/16
(52) U.S. Cl. ...................................... 623/6.46; 623/6.55
(58) Field of Search ................................ 623/6.38–6.55

(56) References Cited

U.S. PATENT DOCUMENTS

| | | | | |
|---|---|---|---|---|
| 4,296,501 A | * | 10/1981 | Kelman | 623/6.43 |
| 4,468,820 A | | 9/1984 | Uhler et al. | 3/13 |
| 4,504,981 A | * | 3/1985 | Walman | 623/6.54 |
| 4,589,147 A | * | 5/1986 | Nevyas | 623/6.54 |
| 4,608,049 A | * | 8/1986 | Kelman | 623/6.46 |
| 4,629,462 A | * | 12/1986 | Feaster | 623/6.51 |
| 4,676,794 A | * | 6/1987 | Kelman | 623/6.54 |
| 4,781,718 A | | 11/1988 | Lindstrom | 623/6 |
| 4,786,445 A | | 11/1988 | Portnoy et al. | 264/1.4 |
| 4,834,751 A | | 5/1989 | Knight et al. | 623/6 |
| 4,847,020 A | | 7/1989 | Akhavi | 264/2.2 |
| 4,888,013 A | | 12/1989 | Ting et al. | 623/6 |
| 4,955,902 A | | 9/1990 | Kelman | 623/6 |
| 4,964,206 A | | 10/1990 | Knoll et al. | 29/424 |
| 5,047,051 A | | 9/1991 | Cumming | 623/6 |
| 5,133,749 A | * | 7/1992 | Nordan | 623/6.49 |
| 5,523,029 A | | 6/1996 | Korgel | 264/1.37 |
| 5,628,796 A | * | 5/1997 | Suzuki | 623/6.52 |
| 5,683,456 A | | 11/1997 | Blake | 623/6 |
| 5,766,244 A | | 6/1998 | Binder | 623/6 |
| 5,928,282 A | | 7/1999 | Nigam | 623/6 |
| 6,171,337 B1 | * | 1/2001 | Galin | 623/6.11 |

OTHER PUBLICATIONS

Intraocular Lenses, Evolution, Design, Complications, and Pathology, David J. Appple, M.D., Chapter 4, pp. 59–105.

* cited by examiner

Primary Examiner—David J. Isabella
Assistant Examiner—Urmi Chattopadhyay
(74) Attorney, Agent, or Firm—Gardner Groff, P.C.

(57) ABSTRACT

In the connection zone, the portion of the haptic part connected to the optic part is situated on the edge of the optic part. The optic part consists of a flexible lens which can be folded or rolled upon insertion of the implant into the anterior chamber. The haptic part has a general form of the number 2 and has an upper free end, a bend, and a lower free end. In the connection zone, the connection between the optic part and the haptic part is rigid.

10 Claims, 1 Drawing Sheet

ANTERIOR CHAMBER INTRAOCULAR IMPLANT

CROSS-REFERENCE TO RELATED APPLICATIONS

This Application is a continuation of PCT/FR99/02126, file Sep. 7, 1999.

BACKGROUND OF THE INVENTION

The invention relates to an anterior chamber intraocular implant for treating ametropias of the phakic eye. An implant of this type comprises an optic part composed of a circular lens whose mid-plane is perpendicular to the optic axis of the eye, and of a haptic part consisting of a fixture with flexible loops which are lodged in the iridocorneal angle, said haptic part being intended to fix and maintain the position of the optic part in the anterior chamber. The term "flexible" is to be understood as meaning a semi-rigid structure which is capable of giving the assembly of optic part+haptic part a permanent stability in the anterior chamber. However, this flexibility is not such as to permit bending of the haptic part. Such implants are described in documents FR-2 631 228 and FR 2 666 220. As a result of their rigid structure in the optic part, these implants require, for their introduction into the anterior chamber of the eye, a fairly large insertion orifice which must subsequently be sutured.

It is an object of the invention to provide an intraocular implant which can be introduced into the anterior chamber through quite a small orifice so as not to require suturing.

Moreover, the implants in the abovementioned documents have a haptic part which exhibits a certain symmetry.

This haptic part generally comprises four bearing points in the iridocorneal angle, in an arrangement which must be substantially symmetrical. This symmetry must be respected when fitting the implant, and this sometimes lengthens the time of the surgical intervention.

It is another object of the invention to provide an intraocular implant which is not subject to this constraint of symmetry.

BRIEF SUMMARY OF THE INVENTION

The subject of the invention is an anterior chamber intraocular implant composed of a circular optic part and a flexible haptic part for maintaining the optic part in the anterior chamber, the bearing points of the haptic part being lodged in the iridocorneal angle, characterized in that the optic part consists of a flexible lens which can be rolled or folded upon insertion of the implant into the anterior chamber; the haptic part has a zone of connection to the optic part, and in this connection zone the portion of the haptic part connected to the optic part is situated on the edge of the optic part; and, in the connection zone, the connection between the optic part and the haptic part is rigid, so that when the implant is in place, the optic part is maintained stable in a plane perpendicular to the optic axis of the eye.

According to other characteristics:

in the connection zone, the haptic part comprises a rigid portion in order to ensure rigid connection to the optic part;

the haptic part has the general shape of the number 2 and has three bearing points, one at the bend and one at each of the free ends;

the connection zone is situated on the curved loop connecting the bend of the haptic part to the upper free end;

the connection zone is situated on the concave side of the loop of the haptic part;

the connection zone is a zone of tangency between the optic part and the haptic part;

the haptic part has a sort of cradle whose edge is substantially circular so as to be in contact with the lens over an extended connection zone;

the optic part consists of a lens made of acrylic material, silicone or HEMA;

the haptic part is made of PMMA, or of any other material compatible with the eye.

BRIEF DESCRIPTION OF THE SEVERAL VIEWS OF THE DRAWINGS

Other characteristics will become clear from the following description in which reference is made to the attached drawings, in which.

DETAILED DESCRIPTION OF THE INVENTION

Figure 1:
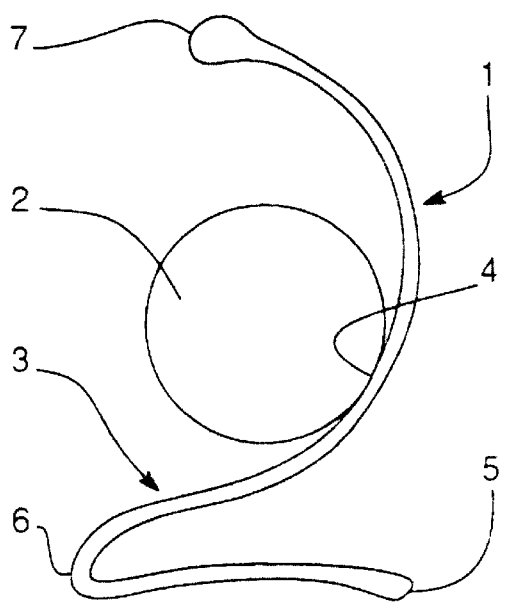
FIG. 1 is a front view of an implant according to one embodiment of the invention.

In FIG. 1, the implant 1 according to the invention consists of an optic part 2 in the form of a circular lens, and of a haptic part 3 having the general shape of the number 2.

The haptic part has three points of contact with the iridocorneal angle: the first at its lower free end 5, the second at its bend 6, and the third at its upper free end 7. In the central portion of the curved loop connecting the bend 6 to the upper free end 7 of the haptic part there is a connection zone 4 between the haptic part 3 and the optic part 2.

In the connection zone 4, the connection between the optic part 2 and the haptic part 3 is rigid so that when the implant 1 is in place, the optic part 2 is maintained stable in a plane perpendicular to the optic axis of the eye. To ensure this rigidity of the connection, the haptic part 3 advantageously has a rigid portion in the connection zone 4.

This stability of orientation of the optic part in the plane perpendicular to the optic axis is indispensable not only for the optical quality but also in respect of the adjoining ocular structures (iris, crystalline lens, cornea) which could be damaged if the optic part were able to move freely toward the rear in relation to the haptic part. This risk would be very great because of the permanent changes in the position of the eyeball.

When the implant 1 is in place in the anterior chamber of the eye (FIG. 2), the optic part 2 is in a plane perpendicular to the optic axis 8 of the eye, and the three points of contact 5, 6, 7 of the haptic part are distributed on the circumference of the iridocorneal angle 9. The optic part 2 preferably comprises a lens whose front face 10 is concave. This concave face 10 is directed toward the crystalline lens 11 and the iris 12 of the eye. The connection between the optic part 2 and the haptic part 3 is made in the connection zone 4 by any suitable means such as bonding, welding, physicochemical connection, or mechanical joining, for example.

Figure 3:
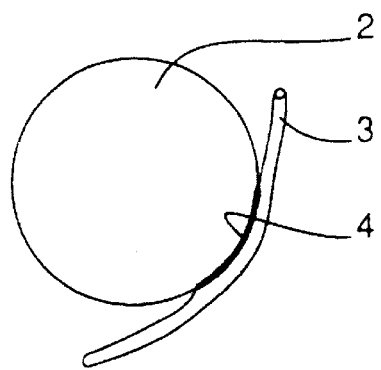
FIG. 3 is a partial front view of the implant in FIG. 1.

The lens of the optic part 2 is arranged on the concave side of the loop of the haptic part in such a way that the connection zone 4 (FIG. 3) is a zone of tangency between the optic part 2 and the haptic part 3.

Figure 4:
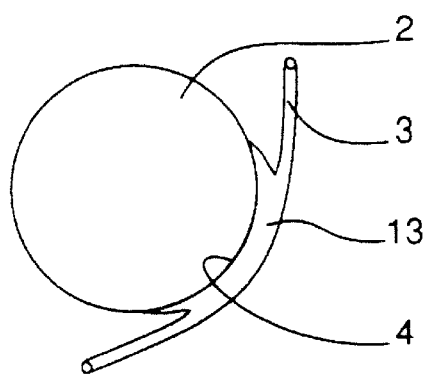
FIG. 4 is a view, analogous to that in FIG. 3, of another embodiment of the implant according to the invention.

According to the embodiment in FIG. 4, the haptic part has a sort of cradle 13 whose edge is substantially circular so as to be in contact with the lens over an extended connection zone 4.

Figure 2:
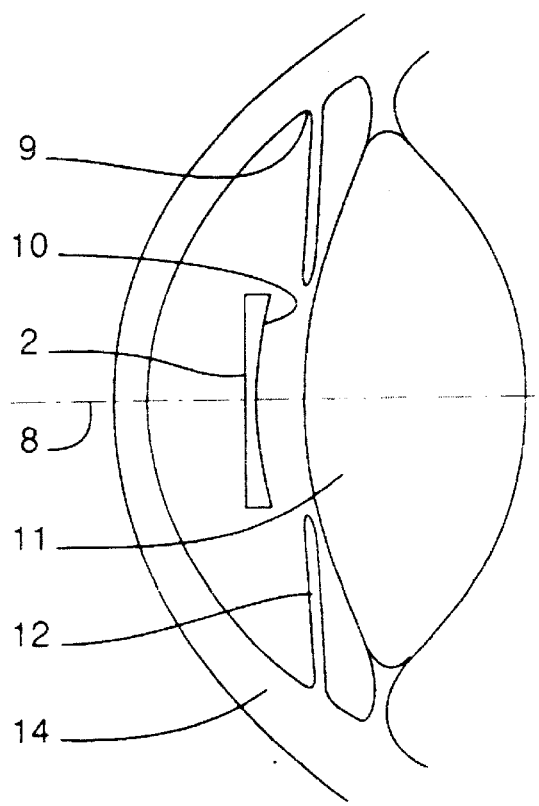
FIG. 2 is a simplified axial cross section of the anterior chamber of an eye fitted with the implant in FIG. 1.

In the connection zone 4, the portion of the haptic part 3 connected to the optic part 2 is situated on the edge of the optic part 2, for example in the mid-plane of the edge of the lens. Outside the connection zone 4, the haptic part 3 can have inclinations relative to the mid-plane of the lens in order to ensure the offset position of the optic part 2 relative to the mid-plane of the iridocorneal angle 9 (FIG. 2). This arrangement ensures that when the implant 1 is in place the connection zone 4 is situated in a plane perpendicular to the optic axis 8 of the eye and maintains the optic part 2 perpendicular to this optic axis 8, in front of the iridal plane.

According to a main characteristic of the invention, the optic part 2 consists of a flexible lens which, for insertion of the implant 1 into the anterior chamber, can be rolled up on itself or about the haptic part in the connection zone 4, the axis of roll being parallel to the mean direction of the haptic part in the connection zone 4.

The lens can also be folded about an axis parallel to the mean direction of the haptic part in the connection zone 4. After insertion of the implant, the flexible lens is released and it recovers its initial shape.

To ensure this flexibility and this elasticity of the lens, the material constituting the lens is for example an acrylic material, silicone, or HEMA.

The material constituting the haptic part 3 is flexible but sufficiently rigid to maintain the optic part 2 in a stable position: PMMA is preferably used.

The implant 1 is inserted into the anterior chamber through an insertion orifice made in the cornea 14. As the flexible lens can be rolled against, or on, the loop of the haptic part 3, or can be folded on the loop of the haptic part 3, the greatest dimension of the insertion orifice is less than or equal to 4 mm, so that this insertion orifice seals automatically and does not need to be sutured, which simplifies the surgical intervention.

The introduction of the implant through the insertion orifice is effected via the lower end 5 of the haptic part, then the bend 6, then the loop of the haptic part on which or against which the optic lens 2 is rolled or folded, and finally via the upper free end 7.

The implant according to the invention can be used for treating an ametropia, for example myopia, hypermetropia or astigmatism. It is necessary merely that the edge of the optic part is thick enough to ensure the connection with the haptic part in the connection zone 4. This condition is particularly easy to fulfil in the case of myopia, since the lens in this case has thick edges.

By way of example, a tripodal anterior chamber intraocular implant according to the invention is intended to be fitted in the circle corresponding to the iridocorneal angle which has a diameter of less than or equal to 13.5 mm. The diameter of the optic part 2 is less than or equal to 6 mm. The loop of the haptic part 3 has a thickness of approximately 0.1 mm. The greatest dimension of the orifice for inserting the implant into the anterior chamber is less than or equal to 4 mm and this orifice is not suturable.

What is claimed is:

1. Anterior chamber intraocular implant for treating ametropias of a phakic eye, comprising an optic part, consisting of a flexible lens which can be rolled or folded upon insertion of the implant into an anterior chamber of the eye, and a flexible haptic part for maintaining the optic part in the anterior chamber, wherein the haptic part has bearing points configured to lodge in the iridocorneal angle, wherein the haptic part comprises a bend, a lower free end, and an upper free end and has the general shape of the number 2; and has three bearing points, one at the bend and one at each of the free ends;

wherein the haptic part is connected to an edge of the optic part at a zone of connection;

wherein in the connection zone, the connection between the optic part and the haptic part is rigid, whereby the optic part is maintained stable in a plane perpendicular to the optic axis of the eye;

wherein the haptic part is curved between the bend and a free end, said curve has a concave side and a convex side;

wherein the connection zone is on the concave side of the curve and is a zone of tangency between the optic part and the haptic part.

2. Implant according to claim 1, wherein the haptic part comprises a rigid portion at the connection zone to ensure rigid connection to the optic part.

3. Implant according to claim 1, wherein the connection zone is between the bend of the haptic part and the upper free end.

4. Implant according to claim 1, wherein the lens is made from a material selected from the group consisting of acrylic material, silicone and HEMA.

5. Implant according to claim 1, wherein the haptic part is made from PMMA.

6. Anterior chamber intraocular implant for treating ametropias of a phakic eye, comprising an optic part, consisting of a flexible lens which can be rolled or folded upon insertion of the implant into an anterior chamber of the eye, and a flexible haptic part for maintaining the optic part in the anterior chamber, wherein the haptic part has bearing points configured to lodge in the iridocorneal angle, wherein the haptic part comprises a bend, a lower free end, and an upper free end and has the general shape of the number 2; and has three bearing points, one at the bend and one at each of the free ends;

wherein the haptic part is connected to an edge of the optic part at a zone of connection and has a cradle whose edge is substantially circular so as to be in contact with the lens over the connection zone;

wherein in the connection zone, the connection between the optic part and the haptic part is rigid, whereby the optic part is maintained stable in a plane perpendicular to the optic axis of the eye; and wherein the haptic part is curved between the bend and a free end, said curve has a concave side and a convex side; wherein the connection zone is on the concave side of the curve.

7. Implant according to claim 6, wherein the haptic part comprises a rigid portion at the connection zone to ensure rigid connection to the optic part.

8. Implant according to claim 6, wherein the connection zone is between the bend of the haptic part and the upper free end.

9. Implant according to claim 6, wherein the lens is made from a material selected from the group consisting of acrylic material, silicone and HEMA.

10. Implant according to claim 6, wherein the haptic part is made from PMMA.

* * * * *